United States Patent
Cheng et al.

(10) Patent No.: US 10,144,006 B2
(45) Date of Patent: Dec. 4, 2018

(54) METHOD AND CATALYST SYSTEM FOR THE PRODUCTION OF PARA-XYLENE

(71) Applicant: ExxonMobil Chemical Patents Inc., Baytown, TX (US)

(72) Inventors: Jane C. Cheng, Bethlehem, PA (US); Xiaobo Zheng, Houston, TX (US); Hari Nair, Somerville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 53 days.

(21) Appl. No.: 14/802,631

(22) Filed: Jul. 17, 2015

(65) Prior Publication Data

US 2016/0059224 A1   Mar. 3, 2016

Related U.S. Application Data

(60) Provisional application No. 62/041,719, filed on Aug. 26, 2014.

(51) Int. Cl.

| | |
|---|---|
| *C07C 5/27* | (2006.01) |
| *B01J 29/04* | (2006.01) |
| *B01J 35/02* | (2006.01) |
| *B01J 19/00* | (2006.01) |
| *B01J 8/04* | (2006.01) |
| *B01J 23/36* | (2006.01) |
| *B01J 29/40* | (2006.01) |
| *B01J 29/80* | (2006.01) |
| *B01J 37/00* | (2006.01) |
| *B01J 37/02* | (2006.01) |

(52) U.S. Cl.
CPC ........... *B01J 35/023* (2013.01); *B01J 8/0453* (2013.01); *B01J 8/0457* (2013.01); *B01J 19/0093* (2013.01); *B01J 23/36* (2013.01); *B01J 29/40* (2013.01); *B01J 29/80* (2013.01); *B01J 37/0018* (2013.01); *B01J 37/0201* (2013.01); *C07C 5/2708* (2013.01); *C07C 5/2724* (2013.01); *C07C 5/2737* (2013.01); *C07C 5/2754* (2013.01); *B01J 2208/00716* (2013.01); *B01J 2208/025* (2013.01); *B01J 2208/027* (2013.01); *B01J 2219/00792* (2013.01); *B01J 2219/00835* (2013.01); *B01J 2219/00873* (2013.01); *B01J 2219/00961* (2013.01); *B01J 2229/32* (2013.01); *C07C 2529/48* (2013.01); *Y02P 20/52* (2015.11)

(58) Field of Classification Search
CPC ........ B01J 29/48; B01J 8/0453; B01J 8/0457; B01J 19/0093; B01J 35/023; B01J 2219/00961; B01J 2219/00792; B01J 2208/025; B01J 2219/00835; B01J 2219/00873; B01J 2208/00716; B01J 2208/027; C07C 5/2737; C07C 5/2754; C07C 5/2708; C07C 5/2724; C07C 2529/48

See application file for complete search history.

(56) References Cited

U.S. PATENT DOCUMENTS

| | | | |
|---|---|---|---|
| 4,899,011 A | 2/1990 | Chu et al. | |
| 5,689,027 A | 11/1997 | Abichandani et al. | |
| 6,028,238 A * | 2/2000 | Beck | C07C 15/067 585/481 |
| 7,247,762 B2 * | 7/2007 | Stern | C07C 5/2724 585/481 |

FOREIGN PATENT DOCUMENTS

| | | |
|---|---|---|
| WO | WO 99/52842 | 10/1999 |

OTHER PUBLICATIONS

Chen et al. (Shape selective catalysis in industrial applications, 1996, Marcel and Dekker, Inc. New York, pp. 19-21).*
Bhatia (Zeolite Catalysis: Principles and Applications, CRC Press, 1990) (Year: 1990).*

* cited by examiner

*Primary Examiner* — Youngsul Jeong
(74) *Attorney, Agent, or Firm* — Siwen Chen

(57) ABSTRACT

A catalyst system is disclosed for producing para-xylene from a $C_8$ hydrocarbon mixture comprising ethylbenzene and at least one xylene isomer other than para-xylene. The catalyst system comprises a first catalyst bed and a second catalyst bed. The first catalyst bed comprises a first zeolite and a rhenium hydrogenation component. The first zeolite has a constraint index from 1 to 12, an average crystal size from 0.1 to 1 micron and has been selectivated to have an ortho-xylene sorption time of greater than 1200 minutes based on its capacity to sorb 30% of the equilibrium capacity of ortho-xylene at 120° C. and an ortho-xylene partial pressure of 4.5±0.8 mm of mercury. The second catalyst bed comprises a second zeolite and a rhenium hydrogenation component. The second zeolite has a constraint index ranging from 1 to 12 and an average crystal size of less than 0.1 micron.

9 Claims, No Drawings

METHOD AND CATALYST SYSTEM FOR THE PRODUCTION OF PARA-XYLENE

PRIORITY CLAIM

This application claims priority to and the benefit of U.S. Provisional Application No. 62/041,719, filed Aug. 26, 2014, the disclosure of which is incorporated herein by reference in its entirety.

FIELD OF THE INVENTION

This invention relates to a catalyst system and process for producing para-xylene.

BACKGROUND OF THE INVENTION

Para-xylene is a valuable chemical feedstock, which may be derived from mixtures of $C_8$ aromatics separated from such raw materials as petroleum naphthas, particularly reformates, usually by selective solvent extraction. The $C_8$ aromatic fractions from these sources vary quite widely in composition but will usually comprise 10 to 32 wt % ethylbenzene (EB) with the balance, xylenes, being divided between approximately 50 wt % of the meta isomer and 25 wt % each of the para and ortho isomers. Of these isomers, para-xylene is by far the most important.

Individual isomer products may be separated from the naturally occurring $C_8$ aromatic mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption (e.g., the Parex process), or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence, an important feature of any commercial xylene isomerization process is the ability to convert ethylbenzene in the feed to useful by-products while simultaneously minimizing any conversion of xylenes to other compounds.

One commercially successful xylene isomerization process is described in U.S. Pat. No. 4,899,011 in which a $C_8$ aromatic feed, which has been depleted in its para-xylene content, is contacted with a two component catalyst system. The first catalyst component selectively converts the ethylbenzene by deethylation, while the second component selectively isomerizes the xylenes to increase the para-xylene content to a value at or approaching the thermal equilibrium value. The first catalyst component comprises a Constraint Index 1 to 12 zeolite, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1 to 12 zeolite which has an ortho-xylene sorption time of less than 10 minutes under the same conditions. In one preferred embodiment, the first catalyst component is ZSM-5 having a crystal size of at least 1 micron and the second catalyst component is ZSM-5 having a crystal size of 0.02 to 0.05 micron. Each catalyst component also contains a hydrogenation metal, preferably a noble metal such as platinum or palladium.

An improvement over the process of U.S. Pat. No. 4,899,011 is described in U.S. Pat. No. 5,689,027 in which the first catalyst component in the two component system is preselectivated by coking, or more preferably by deposition of a surface coating of silica, to increase its ortho-xylene sorption time to greater than 1200 minutes under the same test conditions as cited in the '011 patent. Using such a system it is found that high ethylbenzene conversion rates can be achieved with significantly lower xylene losses than obtained with the process of the '011 patent. Again, the catalyst components employed in the process of the '027 patent include a hydrogenation metal, such as Fe, Co, Ni, Ru, Rh, Pd, Os, Ir, Pt, Mn, Re, Cu, Ag, Au, Cr, Mo, W, Ga, In and Bi, preferably Pt.

In addition to potential xylene loss especially at high ethylbenzene conversion, the two component xylene isomerization/ethylbenzene dealkylation processes described above pose a number of additional concerns. For example, it is important that the hydrogenation metal, particularly that associated with the first catalyst component, provides excellent selectivity for ethylene saturation without saturating benzene such that the benzene fraction after distillation from the final product meets the 99.9 wt % benzene purity specification. In addition, it is important that the catalyst components are resistant to sulfur poisoning and the CO-induced metal migration that can occur on start-up. Developing a catalyst system and operating process that achieves all these requirements remains an area of ongoing research.

SUMMARY OF THE INVENTION

The present invention is directed to a catalyst system for producing para-xylene from a $C_8$ hydrocarbon mixture comprising ethylbenzene and at least one xylene isomer other than para-xylene. The catalyst system comprises a first catalyst bed (1) and a second catalyst bed (2). The first catalyst bed (1) contains a first catalyst comprising a first zeolite having a constraint index ranging from 1 to 12 and an average crystal size from 0.1 to 1 micron and a hydrogenation component comprising rhenium. The first zeolite is selectivated so as to have an ortho-xylene sorption time of greater than 1200 minutes based on its capacity to sorb 30% of the equilibrium capacity of ortho-xylene at 120° C. and an ortho-xylene partial pressure of 4.5±0.8 mm of mercury. The second catalyst bed (2) contains a second catalyst comprising a second zeolite having a constraint index ranging from 1 to 12 and an average crystal size of less than 0.1 micron and a hydrogenation component comprising rhenium. The second zeolite has an ortho-xylene sorption time of less than 50 minutes based on its capacity to sorb 30% of the equilibrium capacity of ortho-xylene at 120° C. and an ortho-xylene partial pressure of 4.5±0.8 mm of mercury.

The invention further provides a process for producing para-xylene from a $C_8$ hydrocarbon mixture comprising ethylbenzene and at least one xylene isomer other than para-xylene. A $C_8$ hydrocarbon mixture is contacted under ethylbenzene conversion conditions with a first catalyst comprising a first zeolite and a hydrogenation component comprising rhenium, such as that described above, to form an ethylbenzene depleted product. The ethylbenzene depleted product is then contacted under xylene isomerization conditions with a second catalyst comprising a second zeolite and a hydrogenation component comprising rhenium, such as that described above, to convert the mixed xylene components of the feed containing para-xylene in an amount less than that at thermal equilibrium to an extent such that product from the isomerizer contains para-xylene in an amount at least approaching that at thermal equilibrium.

DETAILED DESCRIPTION

The present invention is directed to a catalyst system and process for converting high percentages of the ethylbenzene present in mixed ethylbenzene-xylene containing feeds, while simultaneously minimizing xylene loss and aromatics saturation and converting xylenes to approximately the thermal equilibrium concentration. In this way, the volume of any recycle stream and/or complexity of the separation processes needed in a xylene recovery process are minimized and a high purity benzene by-product is produced. In addition, the catalyst system is resistant to sulfur poisoning and the CO-induced metal migration that can occur on start-up.

As used herein, the numbering scheme for the Periodic Table Groups is the current INPAC numbering scheme.

Feedstock

In general, any aromatic $C_8$ mixture containing ethylbenzene and at least one xylene isomer other than para-xylene may be used as feed to the process of this invention. In some embodiments, such a mixture may have an ethylbenzene content in the approximate range of 5 to 60 wt %, an ortho-xylene content in the approximate range of 0 to 35 wt %, a meta-xylene content in the approximate range of 20 to 95 wt % and a para-xylene range of about 0 to 15 wt %. In one embodiment, the feed may contain about 8 to 15 wt % ethylbenzene.

In addition to the above aromatic $C_8$ mixture, the feed may contain non-aromatic hydrocarbons, i.e., naphthenes and paraffins, in an amount up to about 30 wt %. The present catalyst may have high activity for cracking of normal and branched paraffins of the type present in commercial unextracted $C_8$ mixture streams.

In one embodiment, the present process provides means to convert a mixture of $C_8$ aromatics such as that derived from catalytic reforming of a petroleum naphtha to a mixture of reduced ethylbenzene content and increased content of para-xylene. The process is particularly effective in treating a para-xylene lean mixture of $C_8$ aromatics to increase the para-xylene concentration up to approximately the thermal equilibrium level.

Catalyst System

The catalyst system used in the present process includes a first ethylbenzene conversion catalyst and a second xylene isomerization catalyst. As their names suggest, the first catalyst has the primary function of selectively converting the ethylbenzene in the feedstream, preferably by dealkylation, to benzene and $C_2$ components, while the second catalyst component selectively isomerizes xylenes in the feed. The first catalyst component can, and preferably will, effect some isomerization of the xylenes in the feed.

Each of the first and second catalyst components comprises a molecular sieve and a hydrogenation metal or metal compound.

In one embodiment, the molecular sieve of each of the first and second catalyst components is an intermediate pore size molecular sieve having a Constraint Index, before any selectivation, of about 1 to about 12 (e.g., having a pore size less than about 7 Angstroms, such as from about 5 to less than 7 Angstroms). The method by which a Constraint Index is determined is described fully in U.S. Pat. No. 4,016,218, incorporated herein by reference for details of the method. Suitable intermediate pore size molecular sieves are those having the structure types MFI, MEL, MTW, TON, MTT, FER, and MFS using the designations adopted by the IUPAC Commission on Zeolite Nomenclature. Conveniently, the molecular sieves are aluminosilicate forms having a silica/alumina molar ratio of at least 12. Examples of intermediate pore size molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449; ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780), with ZSM-5 being particularly preferred. The entire contents of the above patents are incorporated by reference herein.

The molecular sieve of each of the first and second catalyst components also contains rhenium as a hydrogenation metal. In most embodiments, the rhenium will be the only hydrogenation metal present in each catalyst component, but in some embodiments, other hydrogenation metals may also be present in addition to rhenium. Suitable additional hydrogenation metals include Group 8-10 metals (i.e., Pt, Pd, Ir, Rh, Os, Ru, Ni, Co, and Fe), Group 6 metals (i.e., Cr, Mo, W), Group 14 metals (i.e., Sn and Pb), Group 15 metals (i.e., Sb and Bi), and other Group 7 metals (i.e., Mn and Tc). It is to be appreciated that the hydrogenation metal is not necessarily present on the catalyst in the free metal (i.e., zero valent) form, but can also be present as a compound, such as an oxide, hydroxide or sulfide, of the metal. The metal is typically in an oxidized valence state, e.g., when this component is in the form of an oxide or hydroxide. The reduced valence state of the metal may be attained, in situ, prior to or during the course of a reaction, when a reducing agent, such as hydrogen, is included in the feed to the reactor(s).

The hydrogenation metal may be incorporated into the catalyst by methods known in the art, such as ion exchange, impregnation or physical admixture. For example, solutions of appropriate metal salts may be contacted with the remaining catalyst components under conditions sufficient to combine the respective components. The metal containing salt is preferably water soluble. Examples of suitable salts for the incorporation of rhenium in the catalyst components include perrhenate salts, such as ammonium perrhenate. After incorporation of the metal, the catalyst is calcined at a temperature of from about 250 to about 500° C.

The amount of the rhenium present in each of the first and second catalyst components is suitably from about 0.001 to about 10 percent by weight, e.g., from about 0.1 to about 5 percent by weight, e.g., from about 0.1 to about 2 percent by weight.

In practicing the present process, it may be desirable to formulate either or both of the first and second catalyst components with another material resistant to the temperature and other conditions of the process. Such matrix materials include inorganic oxide materials such as clays, silica, and/or metal oxides. The metal oxides may be naturally occurring or in the form of gelatinous precipitates or gels including mixtures of silica and metal oxides. Naturally occurring clays, which can be composited with the molecular sieve include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds, such as silica-alumina-thoria, silica-alumina-zirconia, silica-alumina-magnesia, and silica-magnesia-zirconia. A mixture of these components can also be used. In addition, the molecular sieve can be composited with a zeolitic matrix material using the method described in International Patent Publication No. WO 96/16004, the entire contents of which are incorporated herein by reference.

The relative proportions of molecular sieve component and inorganic oxide matrix on an anhydrous basis may vary widely with the molecular sieve content ranging from between about 1 to about 99 percent by weight and more usually in the range of about 10 to about 80 percent by weight of the dry composite.

The first and second components of the catalyst system of the invention differ from each other in a number of significant respects, which ensure that first component selectively deethylates the ethylbenzene in the feedstream to benzene while the second component selectively isomerizes xylenes in the feed. These differing characteristics include crystal size and xylene diffusional properties as will be discussed in more detail below.

Ethylbenzene Conversion Component

The first catalyst component, which selectively deethylates the ethylbenzene in the feedstream to benzene, is selected so as to have an average crystal size, as determined by election microscopy, from 0.1 to 1 micron. Crystal size may also be expressed in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, The Mathematics of Diffusion, Clarendon Press, pp. 52-56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t'_{0.3}$, the time required for the uptake of 30% capacity of hydrocarbon, is:

$$d = 0.0704 \times t'_{0.3}{}^{1/2}$$

For example, a crystal having a sorption time for 2,2-dimethylbutane at 90° C. and 60 torr hydrocarbon pressure of 7.8 minutes would have a calculated size of 0.20 microns.

In addition, the first catalyst component is selectivated so as to have an ortho-xylene sorption time of greater than 1200 minutes, but generally less than 10,000 minutes based on its capacity to sorb 30% of the equilibrium capacity of ortho-xylene at 120° C. and an ortho-xylene partial pressure of 4.5±0.8 mm of mercury. A suitable ortho-xylene sorption test is described in U.S. Pat. Nos. 4,117,026; 4,159,282; and Re. 31,782; each of which is incorporated by reference herein. In some embodiments, the first catalyst component is selectivated so as to have an ortho-xylene sorption time from 2000 to 5000 minutes, based on its capacity to sorb 30% of the equilibrium capacity of ortho-xylene at 120° C. and an ortho-xylene partial pressure of 4.5±0.8 mm of mercury.

Selectivation of the first catalyst component is conveniently achieved by deposition on the surface of the catalyst particles of a layer of coke and/or an oxide, such as silica, which is inert under the process conditions experienced in use.

Where the first catalyst component is selectivated with silica, this can be effected by subjecting the catalyst to one or more treatments with an organosilicon compound in a liquid carrier, each treatment being followed by calcination of the treated material in an oxygen-containing atmosphere, e.g., air. Such a multiple selectivation procedure is described in U.S. Pat. No. 5,476,823, the entire contents of which are incorporated herein by reference. Where the catalyst to be silica-selectivated includes a binder, it is preferable to employ a non-acidic binder, such as silica.

The organosilicon compound, which is used to selectivate the first catalyst component may, for example, be a silicone, a siloxane, a silane or mixture thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane, or silane compound need not be linear, but may be cyclic, for example, hexamethyl cyclotrisiloxane, octamethyl cyclotetrasiloxane, hexaphenyl cyclotrisiloxane, and octaphenyl cyclotetra-siloxane. Mixtures of these compounds may also be used as preselectivating agents, as may silicones with other functional groups.

Typically, the kinetic diameter of the organosilicon compound that is used to preselectivate the molecular sieve, is larger than the molecular sieve pore diameter, in order to avoid entry of the organosilicon compound into the molecular sieve pores and any concomitant reduction in the internal activity of the molecular sieve.

Suitable organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

The liquid carrier for the organosilicon compound may be an organic compound, such as a linear, branched or cyclic hydrocarbon having five or more, especially seven or more, carbon atoms per molecule, e.g., an alkane, such as heptane, octane, nonane or undecane. The boiling point of the organic compound, e.g., alkane, may be greater than about 70° C. Mixtures of low volatility organic compounds, such as hydrocracker recycle oil, may be employed as carriers. Suitable organic carriers are decane and dodecane.

Following each impregnation with the organosilicon compound, the catalyst is calcined at a ramp rate from about 0.2° C./minute to about 5° C./minute to a temperature greater than 200° C., but below the temperature at which the crystallinity of the molecular sieve is adversely affected.

This calcination temperature will generally be below 600° C. and preferably is within the approximate range of 350 to 550° C. The duration of heating at the calcination temperature may be from 1 to 24 hours, e.g., from 2 to 6 hours.

In addition to, or in place of, silica selectivation, the first catalyst component may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. This contact temperature may be, for example, less than about 650° C. Organic materials, which may be used for this coke selectivation process, encompass a wide variety of compounds including, by way of example, hydrocarbons, such as paraffins, cycloparaffins, olefins, cycloolefins and aromatics; oxygen-containing organic compounds, such as alcohols, aldehydes, ethers, ketones, and phenols; and heterocyclics, such as furans, thiophenes, pyrroles, and pyridines. A hydrogen cofeed may be used to deter the excessive build-up of coke. Further details regarding coke selectivation techniques are provided in U.S. Pat. No. 4,117,026, incorporated by reference herein. By using a combination of silica selectivation followed by coke selectivation, the number of organosilicon impregnation treatments required to achieve a particular xylene diffusivity can be reduced.

In some embodiments, the zeolite of the first catalyst component has an alpha value of at least 100 and typically has an alpha value of about 300 to about 900. Most preferably, the alpha value of the molecular sieve of the first catalyst component is between 500 and 700. Alpha value is a measure of the cracking activity of a catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. In the case of ZSM-5, the desired alpha value can be obtained by using a zeolite having a silica to alumina molar ratio of less than 50, such as less than 30. If necessary, the alpha activity of the catalyst can be adjusted by steaming. Suitable steaming conditions may include a temperature of from about 100° C. to about 800° C., e.g., from about 175° C. to about 550° C., with from about 1% to about 100% steam, e.g., from about 50% to about 100% steam, at a pressure of from about 0.01 psia to about 5000 psia, e.g. from about 14 psia to about 50 psia, and for a duration of about 0.1 to about 200 hours, e.g., from about 0.5 to about 24 hours, e.g., from about 3 to about 6 hours.

The ethylbenzene conversion catalyst may be in the form of particles having a surface to volume ratio of about 80 to <200 inch$^{-1}$, preferably about 100 to 150 inch$^{-1}$. Thus, it has now been found that the ethylbenzene conversion reaction is sensitive to intraparticle (macroporous) diffusion limitations. By selecting the shape and size of the particles of the catalyst such that the surface to volume ratio is within the specified range, it is found that the intraparticle diffusion distance can be decreased without excessively increasing the pressure drop across the first catalyst bed. This assists in reducing the xylene losses accompanying the ethylbenzene conversion in the first catalyst bed, while at the same time increasing the xylene isomerization activity of the catalyst. Producing an ethylbenzene conversion catalyst with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. For example, a cylindrical catalyst particle having a diameter of 1/32 inch and a length of 3/32 inch has a surface to volume ratio of 141, whereas a quadralobed solid extrudate having the external shape disclosed in FIG. 4 of U.S. Pat. No. 4,441,990 and having a maximum cross-sectional dimension of 1/16 inch and a length of 3/16 inch has a surface to volume ratio of 128. A hollow tubular extrudate having an external diameter of 1/10 inch, an internal diameter of 1/30 inch and a length of 3/10 inch has a surface to volume ratio of 136.

In addition, the first catalyst component may have enhanced macroporosity achieved by adding a thermally decomposable organic material to the mix used to extrude the catalyst particles and then calcining the extruded particles to remove the organic material. The thermally decomposable organic material can be any material which is compatible with the extrudable mix used to form the catalyst particles and which is retained within the mass of the extruded catalyst particles, but which can be removed from the catalyst particles by heating to leave macroporous voids within the particles. A suitable organic material is a cellulose such as that sold under the trade name Avicel.

Xylene Isomerization Component

The second component of the catalyst system is effective to isomerize the xylenes of the feed containing $C_8$ aromatics. The second catalyst component conveniently has an ortho-xylene sorption time (as defined above) of less than about 50 minutes, such as less than about 10 minutes. This is typically achieved by using a small crystal size molecular sieve, having an average crystal size of less than 0.1 micron, such as from 0.02 to 0.05 micron, in this component. The molecular sieve of the second component of the catalyst system will typically have an alpha value less than about 300, such as from about 50 to about 250. In the case of ZSM-5, the desired alpha value can be obtained by using a zeolite having a silica to alumina molar ratio of greater than or equal to 50. If necessary, the alpha activity of the catalyst can be adjusted by steaming.

The second component of the catalyst system may be prepared with the use of a thermally decomposable organic material so as to increase its macroporosity. In addition, the size and shape of the particles of the second catalyst component can be selected so as to have a surface to volume ratio of about 80 to <200 inch$^{-1}$, preferably about 100 to 150 inch$^{-1}$.

Process Conditions

The conditions used in the present process are not narrowly defined, but generally will include a temperature of from about 400 to about 1,000° F. (204 to 540° C.), a pressure of from about 0 to about 1,000 psig (100 to 7000 kPa), a weight hourly space velocity (WHSV) of from about 0.5 and about 100 hr$^{-1}$, and a hydrogen, $H_2$, to hydrocarbon, HC, molar ratio of between about 0.1 and about 10. Typical conditions include a temperature of 570 to 900° F. (299 to 482° C.), a pressure from 100 to 600 psig (696 to 4,238 kPa-a), a weight hourly space velocity (WHSV) from 1 to 50 hr$^{-1}$, and a $H_2$/HC mole ratio from 0.5 to 5.

In general, the process is carried out in a fixed bed reactor containing the catalyst system described above. In one embodiment, the first and second components of the catalyst system are located in sequential beds in a single reactor. That is, the component of the catalyst system used in the process of the invention, which is effective for ethylbenzene conversion, forms a first bed, while the other component of the catalyst system, which is effective for xylene isomerization, forms a second bed downstream of the first bed. The feed is suitably cascaded from the first to the second bed without intervening separation of light gases. As an alternative, the first and second beds could be disposed in separate reactors, which, if desired, could be operated at different process conditions. Additional catalyst beds may be provided prior to or after the first and second catalyst components.

After the conversion process, the isomerization product can be treated to isolate para-xylene and/or other desirable xylene(s). Thus, for example, the isomerizate product can be fed to a variety of para-xylene recovery units, such as a crystallizer, a membrane separation unit, or a selective adsorption unit, and thus, the para-xylene may be isolated and recovered. The residual isomerizate can be stripped of products lighter than $C_8$. Products heavier than $C_8$ in the residual isomerizate can be further processed or may be fractionated out. $C_8$ fractions from which para-xylene has been removed can be recycled to the isomerizer.

One result of the process of this invention is to convert the mixed xylene components of the feed containing para-xylene in an amount less than that at thermal equilibrium to an extent such that product from the isomerizer contains para-xylene in an amount at least approaching that at thermal equilibrium.

Another result of the process of this invention is the conversion of a high proportion of the ethylbenzene contained in the mixed xylene feed with minimal xylene loss. For example, ethylbenzene conversion levels of greater than 50 wt % can be accomplished at xylene loss levels of less than 2 wt %. Moreover, the use of rhenium as the hydrogenation metal provides excellent selectivity for ethylene saturation without saturating benzene such that the benzene fraction after distillation from the final product meets the 99.9 wt % benzene purity specification.

The invention will now be more particularly described with reference to the following non-limiting Examples.

Example 1

A catalyst was prepared by extruding ZSM-5 (1-3 micron crystals at 70:1 $SiO_2/Al_2O_3$ ratio) and Versal-300 alumina in 1:1 weight ratio into 1/16" diameter quadrulobe extrudate. The extrudate was calcined in nitrogen at 1000° F. (538° C.) for 3 hours, then exchanged with $NH_4NO_3$ solution followed by further calcination in 8% $O_2$ at 1000° F. (538° C.) for 6 hours. The resultant H-form of the extrudate was steamed at 900° F. (482° C.) for 3 hours, impregnated with ammonium perrhenate solution, air-dried at 250° F. (121° C.) for 4 hours, then calcined in air at 975° F. (524° C.) for 1 hour. The final catalyst contained 0.5 wt % of Re.

Example 2

A catalyst was prepared by extruding ZSM-5 (less than 0.1 micron crystals at 70:1 $SiO_2/Al_2O_3$ ratio) and Versal-300 alumina in 1:1 weight ratio into 1/16" diameter cylindrical extrudate. The extrudate was calcined in nitrogen at 900° F. (482° C.) for 3 hours and then in air at 1000° F. (538° C.) for 6 hours. The calcined extrudate was steamed at 1000° F. (538° C.) for 6 hours, impregnated with ammonium perrhenate solution, air-dried at 250° F. (121° C.) for 4 hours, then calcined in air at 975° F. (524° C.) for 1 hour. The final catalyst contained 0.5 wt % of Re.

Example 3

A catalyst precursor was prepared by extruding a mixture comprising 65 wt % ZSM-5 (having an average crystal size from 0.1 to 1 micron and a 26:1 $SiO_2/Al_2O_3$ molar ratio) and 35 wt % silica binder into a 1/16" diameter cylindrical extrudate form. The extrudate was selectivated using a multiple impregnation treatment with three successive impregnations using 7.8 wt % dimethylphenylmethyl polysiloxane (Dow-550) dissolved in decane. After each impregnation, the solvent was stripped from the extrudate and the extrudate was calcined in nitrogen and air at 538° C. The resultant catalyst precursor was tested to determine the time required to sorb ortho-xylene in an amount equal to 30% of the total xylene sorption capacity at 120° C. and 4.5±0.8 mm mercury, $t_{0.3}$. The value of $t_{0.3}$ was 3600 minutes.

50 g of this catalyst precursor was humidified overnight. An impregnation solution made with 0.36 g of ammonium perrhenate and 14.5 g of de-ionized water was slowly added to the humidified precursor. The mixture was tumbled thoroughly until completely loose. The catalyst was dried at ambient conditions, then in air at 250° F. (121° C.) for 4 hours and thereafter was calcined at 660° F. (349° C.) for 3 hours with a mixture of 40% air and 60% nitrogen. The final catalyst contained 0.5 wt % of Re.

Example 4

A mixture of 1831 g of H-ZSM-5 (less than 0.1 micron crystals and $SiO_2/Al_2O_3$ molar ratio=70:1) and 540 g Versal 300 was mulled thoroughly in a muller. An 1196 g of de-ionized water was added to the mixture while mulling. The mixture was then extruded with a 1/16" cylinder die plate. The extrudate was dried at 250° F. (121° C.) and cracked into short lengths (about 0.5 inch long).

A portion of the extrudate, 2000 cc, was heated in flowing nitrogen (5 vol/vol/min) at a ramp rate of 150° F./h (83° C./hr) to 900° F. (482° C.), and then held at 900° F. (482° C.) for 3 hr. While at 900° F. (482° C.), the gas mixture was changed to 0.25 vol/vol/min air+4.75 vol/vol/min nitrogen, hold for 30 min; 0.50 vol/vol/min air+4.50 vol/vol/min nitrogen, hold for 30 min; 1.0 vol/vol/min air+4.0 vol/vol/min nitrogen, hold for 30 min; 2.0 vol/vol/min air+3.0 vol/vol/min nitrogen, hold for 30 min. The temperature was then increased at 150° F./h (83° C./hr) to 1000° F. (538° C.). Once at 1000° F. (538° C.), the gas mixture was changed to 4 vol/vol/min air+1 vol/vol/min nitrogen then held for 6 hours. The catalyst was cooled down to ambient conditions.

The calcined catalyst was then steamed by initially heating the catalyst in flowing nitrogen while ramping at 150° F./h (83° C./hr) to 900° F. (482° C.), then holding at 900° F. (482° C.) for 30 min. The flow was switched to 100% steam over a 30 min period. The temperature was increased at 150° F./h (83° C./hr) to 950° F. (510° C.), and then held for 4 hours in 100% steam. The catalyst was cooled down in air.

A 50 g portion of the steamed catalyst was humidified overnight. An impregnation solution made with 0.36 g of ammonium perrhenate and 27 g of de-ionized water was slowly added to the humidified catalyst. The mixture was tumbled thoroughly until completely loose. The catalyst was dried at ambient conditions then in air at 250° F. (121° C.) for 4 hours. The catalyst was then calcined at 750° F. (399° C.) for 6 hours with a mixture of 40% air and 60% nitrogen. The final catalyst contained 0.5 wt % of Re.

Example 5

The process of Example 3 was repeated but, after drying the rhenium-impregnated catalyst at 250° F. (121° C.) for 4 hours in air, the catalyst was calcined in air at 975° F. (524° C.) for 1 hour.

Example 6

The process of Example 4 was repeated but, after drying the rhenium-impregnated catalyst at 250° F. (121° C.) for 4 hours in air, the catalyst was calcined in air at 975° F. (524° C.) for 1 hour.

Example 7

A fixed bed, down-flow reactor with ⅜" external diameter was used to evaluate the performance of a dual bed catalyst system comprising the catalysts as prepared in Examples 1 and 2. The reactor was equipped with a ⅛" diameter thermal well to monitor reactor temperature at the center of the catalyst bed. The catalysts were loaded into the reactor as indicated below.

| Catalyst | Catalyst form | Catalyst Wt, g |
|---|---|---|
| Top Bed, Example 1 | 1/16" quadrulobe extrudate | 0.7 |
| Bottom Bed, Example 2 | 1/16" cylindrical extrudate | 1.3 |

The reactor pressure was set at 225 psig (1652 kPa-a) with a steady flow of $H_2$ at 92 cc/min. The reactor temperature was increased at 0.833° C./min to 200° C., and held at 200° C. for 16 hours to dry the catalyst. The temperature was further increased at 0.833° C./min to 380° C., and held at 380° C. for 3 hours to reduce the metal. A feed having the composition shown in Table 1 and a density of 0.87 g/cc was introduced into the reactor at 27.6 cc/hr (12 WHSV). This feed rate was maintained through the entire run. The reactor pressure was then decreased to 185 psig (1377 kPa-a), the $H_2$ flow was reduced to 82 cc/min, and reactor temperature was increase at 0.833° C./min to 430° C., and held at 430° C. for 24 hours to de-edge the catalyst.

The reactor pressure was increased to 225 psig (1652 kPa-a), the $H_2$ flow was increased to 92 cc/min, and reactor temperature was reduced to 340° C., and held for 12 hours at 340° C. for data collection by an online GC. The reactor temperature was further increased at 0.833° C./min to 390, 410, 430, and 450° C. consecutively and held for 12 hours at each temperature for data collection by online GC. The results are shown in Table 1.

Example 8

The catalysts of Examples 3 and 4 were loaded into the reactor employed in Example 7 as indicated below.

| Catalyst | Catalyst form | Catalyst Wt, g |
|---|---|---|
| Top Bed, Example 3 | 1/16" cylindrical extrudate | 0.5 |
| Bottom Bed, Example 4 | 1/16" cylindrical extrudate | 1.5 |

The same start-up procedure described in Example 7 was used. The catalysts were tested at 340, 355, 370, 385, and 400° C. at 12 WHSV and 1:1 $H_2$/HC ratio. The results are shown in Table 1.

Example 9

The catalysts of Examples 5 and 6 were loaded into the reactor employed in Example 7 as indicated below.

| Catalyst | Catalyst form | Catalyst Wt, g |
|---|---|---|
| Top Bed, Example 5 | 1/16" cylindrical extrudate | 0.5 |
| Bottom Bed, Example 6 | 1/16" cylindrical extrudate | 1.5 |

The same start-up procedure described in Example 7 was used. The catalysts were tested at 340, 355, 370, 385, and 400° C. at 12 WHSV and 1:1 $H_2$/HC ratio. The results are shown in Table 1.

TABLE 1[1]

| | | Example | | |
|---|---|---|---|---|
| | (feed) | 7 | 8 | 9 |
| Temperature, ° F. | | 798 | 737 | 725 |
| Temperature, ° C. | | 426 | 392 | 385 |
| EB Conversion, % | | 75.6 | 75.2 | 75.4 |
| Product Distribution, wt % | | | | |
| $H_2$ | 0.000 | −0.167 | −0.147 | −0.141 |
| $C_5^-$ (light hydrocarbons) | 0.000 | 2.794 | 2.527 | 2.459 |
| $C_6^+$ Non-aromatics | 0.925 | 0.602 | 0.688 | 0.697 |
| $C_9^+$ Aromatics | 0.031 | 1.330 | 1.278 | 1.054 |
| Benzene | 0.007 | 6.244 | 6.165 | 6.182 |
| Toluene | 0.401 | 3.168 | 2.483 | 2.187 |
| p-Xylene | 2.264 | 19.836 | 20.157 | 20.294 |
| o-Xylene | 18.612 | 19.163 | 19.092 | 19.119 |
| m-Xylene | 65.473 | 44.034 | 44.708 | 45.130 |
| EB | 12.287 | 2.997 | 3.050 | 3.019 |
| Total | 100.00 | 100.00 | 100.00 | 100.00 |
| Total Xylenes | 86.350 | 83.033 | 83.956 | 84.543 |
| $C_2/C_2^-$, Molar ratio | | 2028 | 1924 | 1950 |
| Xylene loss[2], wt % | | 3.30 | 2.67 | 2.20 |
| Ring loss[3], mole % | | −0.17 | −0.20 | −0.24 |
| PXAE[4] | | 102.14 | 102.15 | 102.02 |
| Benzene Sel from EB[5], % | | 91.29 | 90.64 | 90.56 |
| Benzene Purity, % | | 99.83 | 99.92 | 99.90 |

[1]Test conditions: 230 psig total pressure, 12 WHSV, 1:1 $H_2$/HC, ~70 hr on stream.
[2]Xylene loss = 100 × (feed xylene − product xylene)/feed xylene.
[3]Ring loss = 100 × (total aromatic carbon in feed − total aromatic carbon in products)/total aromatic carbon in feed.
[4]PXAE: p-Xylene approaching equilibrium.
[5]Benzene Selectivity from EB = 100 × (Product benzene − Feed benzene)/(Feed EB-Product EB).

Table 1 shows the micro reactor test results at 75% ethylbenzene (EB) conversion. When compared with catalysts used in Example 7, the catalysts used in Examples 8 and 9 were significantly more active: the Example 7 catalysts required 426° C. to achieve 75% EB conversion; whereas the catalysts of Examples 8 and 9 required 392° C. and 385° C. respectively for 75% EB conversion. The lower temperature operation in Examples 8 and 9 provided higher total xylenes (84-84.5% vs. 83%), lower $C_5^-$ hydrocarbons (2.5% vs. 2.8%), lower xylene loss (2.2-2.8% vs. 3.3%), lower benzene (6.17-6.18 vs. 6.24%), lower toluene (2.2-2.5% vs. 3.2%), and lower $C_9^+$ aromatics (1.05-1.28% vs. 1.33%). When compared with Example 8, Example 9 offered additional advantages over Example 8 in terms of activity and overall selectivity. This indicates that final calcination at 975° F. for 1 hour as described in Examples 5 and 6 produced better catalysts.

Example 10

The catalysts of Examples 1 and 2 were loaded into a pilot reactor as indicated below.

| Catalyst | Catalyst form | Catalyst Wt, g |
|---|---|---|
| Top Bed, Example 1 | 1/16" quadrulobe extrudate | 8.0 |
| Bottom Bed, Example 2 | 1/16" cylindrical extrudate | 8.0 |

The same start-up procedure described in Example 7 was used. Before introducing the feed (see composition in Table 1) the catalysts were sulfided with $H_2S$ (400 ppm in $H_2$) for 150 min to achieve $H_2S$/Re molar ratio of 2:1. The catalysts were tested at temperature to achieve 80% ethylbenzene conversion. The results are shown in Table 2.

Example 11

The catalysts of Examples 5 and 6 were loaded into a pilot reactor as indicated below.

| Catalyst | Catalyst form | Catalyst Wt, g |
|---|---|---|
| Top Bed, Example 5 | 1/16" cylindrical extrudate | 5 |
| Bottom Bed, Example 6 | 1/16" cylindrical extrudate | 15 |

The same start-up procedure described in Example 7 was used. Before introducing the feed (see composition in Table 1) the catalysts were sulfided with $H_2S$ (400 ppm in $H_2$) for 150 min to achieve $H_2S$/Re molar ratio of 2:1. The catalysts were tested at temperatures to achieve 70, 75, and 80% ethylbenzene conversion. The results are shown in Table 2.

TABLE 2[1]

| | Example | | | |
|---|---|---|---|---|
| | 10 | 11 | | |
| Average Reactor Temp., ° F. | 808 | 725 | 735 | 748 |
| Pressure, psig | 281 | 233 | 233 | 233 |
| $H_2$ partial pressure, psia | 141 | 125 | 125 | 125 |
| EB Conversion, % | 79 | 71 | 75 | 80 |
| Product Distribution, wt % ($H_2$-adjusted) | | | | |
| $C_5^-$ (light hydrocarbons) | 3.4 | 2.7 | 2.9 | 3.0 |
| $C_6^+$ Non-aromatics | 0.5 | 0.3 | 0.3 | 0.5 |
| $C_9^+$ Aromatics | 1.3 | 1.1 | 1.2 | 1.3 |
| Benzene | 6.6 | 5.8 | 6.1 | 6.4 |
| Toluene | 3.1 | 1.8 | 2.0 | 2.4 |
| p-Xylene | 19.9 | 20.4 | 20.3 | 20.2 |
| o-xylene | 19.1 | 19.3 | 19.3 | 19.2 |
| m-xylene | 43.7 | 45.4 | 45.1 | 44.7 |
| EB | 2.6 | 3.5 | 3.0 | 2.5 |
| Total | 100 | 100 | 100 | 100 |
| Xylene loss[2], wt % | 3.18 | 1.94 | 2.24 | 2.74 |
| Ring loss[3], mole % | 0.22 | −0.12 | −0.06 | 0.08 |
| $C_2/C_2^=$, Molar ratio | 514 | 794 | 792 | 735 |
| PXAE[4] | 103 | 102 | 102 | 102 |
| Benzene Purity, % | 99.9 | 99.9 | 99.9 | 99.9 |

[1]Test conditions: 15 WHSV, 1:1 $H_2$/HC.
[2]Xylene loss = 100 × (feed xylene − product xylene)/feed xylene.
[3]Ring loss = 100 × (total aromatic carbon in feed − total aromatic carbon in products)/total aromatic carbon in feed.
[4]PXAE: p-Xylene approaching equilibrium.

Table 2 shows the pilot reactor test results. When compared at 80% EB conversion, the catalysts used in Example 11 were 60° F. more active: they required 748° F. vs. 808° F. for Example 10. When compared with Example 10, the lower temperature operation in Examples 11 provided lower $C_5^-$ hydrocarbons (3.0% vs. 3.4%), lower xylene loss (2.7% vs. 3.2%), lower ring loss (0.08% vs. 0.22%), and higher $C_2/C_2^=$ (735 vs. 514).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A process for producing para-xylene from a $C_8$ hydrocarbon mixture comprising ethylbenzene and at least one xylene isomer other than para-xylene, the process comprising:
   (a) contacting the $C_8$ hydrocarbon mixture under ethylbenzene conversion conditions with a first catalyst, comprising a first zeolite comprising ZSM-5 and a hydrogenation component consisting essentially of rhenium, to form a xylene rich product that is depleted in ethylbenzene, wherein the first zeolite has an average crystal size from 0.1 to 1 micron and an alpha value of from greater than 500 to 700, and wherein the first zeolite has been selectivated with organosilicon compounds so as to have an ortho-xylene sorption time of greater than 1200 minutes based on its capacity to sorb 30% of the equilibrium capacity of ortho-xylene at 120° C. and an ortho-xylene partial pressure of 4.5±0.8 mm of mercury, wherein the first catalyst comprises a silica binder; and
   (b) contacting the xylene rich product that is depleted in ethylbenzene under xylene isomerization conditions with a second catalyst comprising a second zeolite comprising ZSM-5 and a hydrogenation component consisting essentially of rhenium, to obtain a para-xylene product, wherein the second zeolite has a constraint index ranging from 1 to 12, an average crystal size of less than 0.1 micron, and an alpha value of from greater than 100 to less than 300, and wherein the second zeolite has an ortho-xylene sorption time of less than 50 minutes based on its capacity to sorb 30% of the equilibrium capacity of ortho-xylene at 120° C. and an ortho-xylene partial pressure of 4.5±0.8 mm of mercury,
   wherein the ethylbenzene conversion conditions comprise a temperature less than about 750° F. (399° C.).
2. The process of claim 1, wherein the ethylbenzene conversion conditions comprise a pressure from 0 to 1,000 psig (100 to 7,000 kPa-a), a weight hourly space velocity (WHSV) from 0.5 to 100 $hr^{-1}$, and a $H_2$/HC mole ratio from 0.1 to 10.
3. The process of claim 1, wherein the xylene isomerization conditions comprise a temperature from 570 to 900° F. (299 to 482° C.), a pressure from 100 to 600 psig (696 to 4,238 kPa-a), a weight hourly space velocity (WHSV) from 1 to 50 $hr^{-1}$, and a $H_2$/HC mole ratio from 0.5 to 5.
4. The process of claim 1, wherein the second zeolite has an average crystal size of from 0.02 to 0.05 micron.
5. The process of claim 1, wherein the first zeolite has been selectivated so as to have an ortho-xylene sorption time from 2,000 to 5,000 minutes based on its capacity to sorb 30% of the equilibrium capacity of ortho-xylene at 120° C. and an ortho-xylene partial pressure of 4.5±0.8 mm of mercury.
6. The process of claim 1, wherein the first zeolite has been selectivated by multiple treatments each comprising contacting the first zeolite with an organosilicon selectivating agent to obtain a selectivated first zeolite and subsequently calcining the selectivated first zeolite.

7. A process for producing para-xylene from a C$_8$ hydrocarbon mixture comprising ethylbenzene and at least one xylene isomer other than para-xylene, the process comprising:

(a) contacting the C$_8$ hydrocarbon mixture under ethylbenzene conversion conditions with a first catalyst, comprising a first zeolite comprising ZSM-5 and a hydrogenation component comprising rhenium, to form a xylene rich product that is depleted in ethylbenzene, wherein the first zeolite has an average crystal size from 0.1 to 1 micron, an alpha value of from greater than 500 to 700, and a silica to alumina molar ratio of less than 50, and wherein the first zeolite has been selectivated with organosilicon compounds so as to have an ortho-xylene sorption time of greater than 1200 minutes based on its capacity to sorb 30% of the equilibrium capacity of ortho-xylene at 120° C. and an ortho-xylene partial pressure of 4.5±0.8 mm of mercury, wherein the first catalyst comprises a silica binder; and (b) contacting the xylene rich product that is depleted in ethylbenzene under xylene isomerization conditions with a second catalyst comprising a second zeolite comprising ZSM-5 and a hydrogenation component comprising rhenium, to obtain a para-xylene product, wherein the second zeolite has a constraint index ranging from 1 to 12, an average crystal size of less than 0.1 micron, an alpha value from 100 to less than 300, and a silica to alumina molar ratio of greater than or equal to 50, and wherein the second zeolite has an ortho-xylene sorption time of less than 50 minutes based on its capacity to sorb 30% of the equilibrium capacity of ortho-xylene at 120° C. and an ortho-xylene partial pressure of 4.5±0.8 mm of mercury, wherein the ethylbenzene conversion conditions comprise a temperature less than about 750° F. (399° C.).

8. The process of claim 7, wherein the silica to alumina molar ratio of the first zeolite is less than 30.

9. The process of claim 1, wherein the second zeolite has an alpha value of about 100.